United States Patent [19]
Öhlschläger et al.

[11] Patent Number: 4,749,643
[45] Date of Patent: Jun. 7, 1988

[54] PHOTOGRAPHIC RECORDING ELEMENT CONTAINING A UV ABSORBENT AND A SILVER HALIDE EMULSION LAYER

[75] Inventors: Hans Öhlschläger, Bergisch Gladbach; Hans Langen, Bonn; Johannes Sobel, Leverkusen, all of Fed. Rep. of Germany

[73] Assignee: Agfa Gevaert Aktiengesellschaft, Leverkusen, Fed. Rep. of Germany

[21] Appl. No.: 898,625

[22] Filed: Aug. 21, 1986

[30] Foreign Application Priority Data

Sep. 3, 1985 [DE] Fed. Rep. of Germany ....... 3531383

[51] Int. Cl.$^4$ .............................................. G03C 5/24
[52] U.S. Cl. .................................... 430/512; 430/931; 558/397; 558/426; 558/430
[58] Field of Search ................ 430/512, 931; 558/430, 558/426, 397

[56] References Cited

U.S. PATENT DOCUMENTS

| | | | |
|---|---|---|---|
| 3,168,550 | 2/1965 | Blumenthal | 558/430 |
| 3,408,367 | 10/1968 | Andreades | 558/430 |
| 3,649,276 | 3/1972 | Sano et al. | 430/512 |
| 3,694,247 | 9/1972 | Desjarlais | 430/931 |
| 3,869,493 | 3/1975 | Bozzato et al. | 558/430 |
| 4,431,726 | 2/1984 | Kojima et al. | 430/512 |
| 4,456,681 | 6/1984 | Kadowaki et al. | 430/512 |
| 4,614,709 | 9/1986 | Sasaki et al. | 430/512 |

*Primary Examiner*—Jack P. Brammer
*Attorney, Agent, or Firm*—Connolly and Hutz

[57] ABSTRACT

Compounds with the structural unit

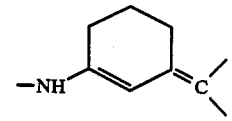

are very valuable UV absorbents, especially in photographic recording materials.

3 Claims, No Drawings

PHOTOGRAPHIC RECORDING ELEMENT CONTAINING A UV ABSORBENT AND A SILVER HALIDE EMULSION LAYER

This invention relates to a photographic recording material containing at least one UV absorbent and to new UV absorbents.

The introduction of UV absorbents into photographic recording materials, in particular into silver halide materials, is known. The UV absorbents prevent the undesirable effect of UV light on exposure or by electrostatic discharges. UV absorbents may be introduced into the recording material, for example as solutions in an oil former such as tricresylphosphate, but this entails considerable disadvantages. DE-A No. 2 541 267 and U.S. Pat. No. 4,045,229, for example, disclose aminoallylidene malodinitriles as UV absorbents for photographic recording materials, but these readily tend to form aggregates resulting in an undesirably broad absorption band with low absorption. The flanks of the absorption band extending right into the blue-sensitive spectral region cause yellow discolouration of the completed image and reduced blue-sensitivity of the recording material. It has been attempted to solve this problem by introducing the UV absorbent in a finely divided form into a so-called loaded latex, see DE-A Nos. 2 541 230 and 2 541 274. The use of polymeric UV absorbents has been disclosed, for example in DE-A Nos. 3 313 547 and 3 327 464, U.S. Pat. No. 4,307,184 and DE-A No. 3 401 455. This method of introduction, however, still does not meet all requirements and generally necessitates the use of a very large quantity of emulsifier so that the photographic layers become overloaded with emulsifier. Large quantities of emulsifier not only overload the layers but have other undesirable effects, e.g. insufficient sharpness, foaming during processing, reduction in the breaking strength and bleeding in storage.

It is an object of the present invention to provide an improved photographic recording material containing a UV absorbent and an improved UV absorbent.

A photographic recording material has now been found containing a UV absorbent carrying the following group (1):

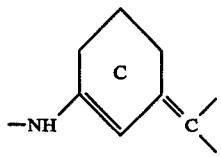

(1)

in which the cyclohexene ring C may be substituted.

In a preferred embodiment, the group (1) forms part of a high molecular weight compound.

In another preferred embodiment, the UV absorbent corresponds to the following formula (2)

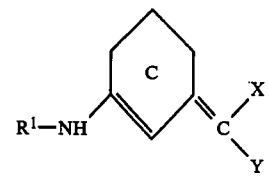

(2)

wherein the cyclohexene ring C may be substituted with the usual substituents used for UV absorbents and $R^1$ denotes a saturated or unsaturated aliphatic hydrocarbon group which may in turn be substituted with the usual substituents for UV absorbents, and X,Y, which may be identical or different, denote an electron accepting group.

In a particularly preferred embodiment. the symbols in formula (2) have the following meaning:

$R^1$ denotes an optionally substituted saturated or unsaturated aliphatic hydrocarbon group with 1 to 24 carbon atoms, which may in turn be substituted, in particular with halogen such as chlorine or bromine, aryl such as phenyl or substituted phenyl, hydroxy, alkoxy such as methoxy, butoxy or hexadecyloxy, aryloxy such as phenoxy or bis-tert.-butylphenoxy or $COOR^5$, X,Y, which may be identical or different, denote CN, $COOR^4$, $CONHR^4$, $COR^4$ or $SO_2R^4$, and $R^4$, $R^5$, which may be identical or different, denote an alkyl group with 1 to 18 carbon atoms or aralkyl with 7 to 15 carbon atoms or an aryl group, and these groups may be substituted or unsubstituted.

In a particularly preferred embodiment X or both X and Y denote a CN group.

UV absorbents corresponding to the following formula (3) are particularly preferred:

$$\begin{array}{c} R^2 \quad R^3 \\ \diagdown \diagup \\ C \\ \diagup \quad \diagdown \\ CH_2 \quad CH_2 \quad CN \\ | \quad | \quad \diagup \\ R^1{-}NH{-}C \quad C{=}C \\ \diagdown \diagup \quad \diagdown \\ CH \quad Y \end{array}$$

(3)

wherein $R^1$ and Y have the meanings indicated above, in particular the preferred meanings. and $R^2$, $R^3$, which may be identical or different, denote hydrogen or an optionally substituted alkyl group with 1 to 4 carbon atoms.

Particularly preferred compounds corresponding to formula (2) are shown in Table 1:

| No. | Formula | |
|---|---|---|
| 1.1 | 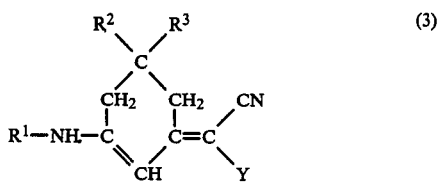 | m.pt. 86° C. |

| No. | Formula | |
|---|---|---|
| 1.2 | 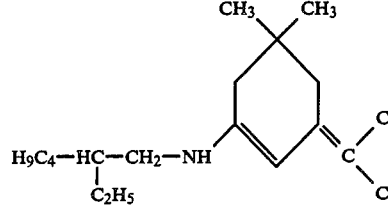 | m.pt. 91–95° C. |
| 1.3 | 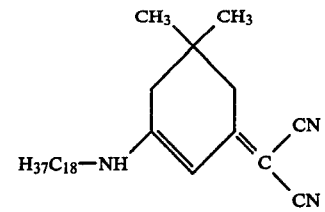 | m.pt. 88–90° C. |
| 1.4 | 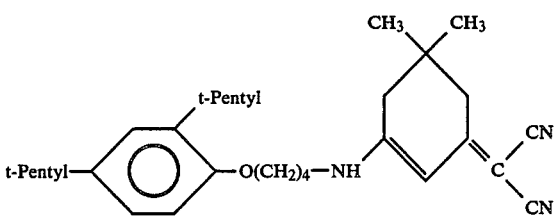 | m.pt. 133–134° C. |
| 1.5 | 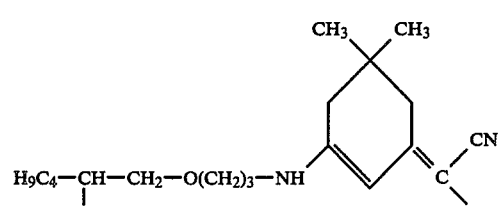 | oil |
| 1.6 | 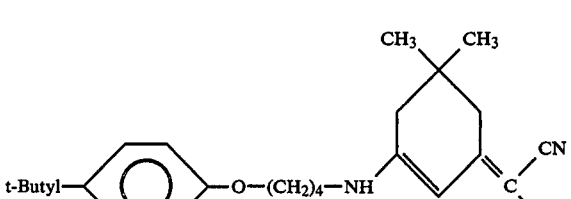 | m.pt. 138–139° C. |
| 1.7 | 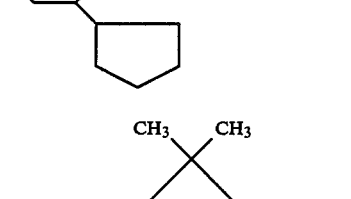 | m.pt. 62–65° C. |
| 1.8 | 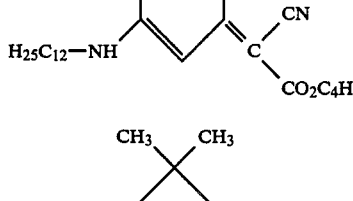 | m.pt. 92–94° C. |

| No. | Formula | |
|---|---|---|
| 1.9 | H$_{25}$C$_{12}$—NH—[cyclohexene]=C(CN)(COOC$_2$H$_5$) | m.pt. 92–94° C. |
| 1.10 | H$_{25}$C$_{12}$—NH—[cyclohexene]=C(CN)(COOC$_4$H$_9$) | m.pt. 61° C. |
| 1.11 | H$_{37}$C$_{18}$—NH—[5,5-dimethylcyclohexene]=C(CN)(COOC$_2$H$_5$) | m.pt. 75–77° C. |
| 1.12 | t-Butyl, t-Butyl-phenyl—O—(CH$_2$)$_4$—NH—[cyclohexene]=C(CN)$_2$ | m.pt. 165–167° C. |
| 1.13 | C$_8$H$_{17}$—HN—[cyclohexene]=C(COOC$_2$H$_5$)(COOC$_2$H$_5$) | |
| 1.14 | C$_4$H$_9$—HN—[cyclohexene]=C(SO$_2$—C$_6$H$_4$—CH$_3$)(COOC$_8$H$_{17}$) | |
| 1.15 | C$_6$H$_{13}$—HN—[5,5-dimethylcyclohexene]=C(COOC$_8$H$_{17}$)(COCH$_3$) | |

| No. | Formula |
|---|---|
| 1.16 | |
| 1.17 | |
| 1.18 | |
| 1.19 | |
| 1.20 | |
| 1.21 | |

The UV absorbent compound corresponding to formula (1) may also form part of a high molecular weight compound HM. In that case, it may be present as group Q having the following structure (4)

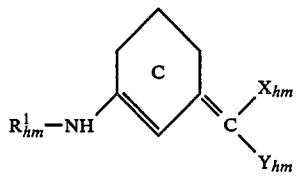
(4)

wherein
$R^1_{hm}$ has the meaning indicated for $R^1$ and
$X_{hm}$, $Y_{hm}$ which may be identical or different, have the meanings indicated under X and Y,
but at least one of the substituents $R^1_{hm}$, $X_{hm}$, $Y_{hm}$ is a chemical bond or a divalent linking member which provides the connection to the high molecular weight compound HM. In a preferred embodiment, the group Q forms part of a polymer corresponding to the following formula (5)

$$\underset{CH_2=C-R^{11}+R^{12}\overline{)_m}+R^{13}\overline{)_n}Q}{\overset{R^{10}}{|}} \quad (5)$$

wherein $R^{10}$ denotes a hydrogen atom, a lower alkyl group with 1 to 4 carbon atoms or a chlorine atom, $R^{11}$ denotes a CONH, COO or phenylene group, $R^{12}$ denotes an alkylene group with 1 to 20 carbon atoms or an arylene group with 6 to 20 carbon atoms, $R^{13}$ denotes a COO, OCO, CONH, NH—CO—O, NHCO, $SO_2NH$, $NHSO_2$ or $SO_2$ group or O, m=0 or a whole number, n=0 or a whole number and Q has the meaning indicated under formula (4).

Specific compounds corresponding to formula (5) are given by way of example in the following Table 2:

| No. | Formula |
|---|---|
| 2.1 | $CH_2=C(CH_3)-COO-(CH_2)_2-HN-$ cyclohexenyl $=C(CN)_2$ |
| 2.2 | $C_2H_5-HN-$ cyclohexenyl $=C(CN)-COO-(CH_2)_2-O-CO-NH-(CH_2)_2-O-CO-C(CH_3)=CH_2$ |
| 2.3 | $CH_2=CH-CO-NH-(CH_2)_2-HN-$ cyclohexenyl $=C(CN)(COOC_2H_5)$ |
| 2.4 | $CH_2=CH-COO-(CH_2)_2-HN-$ (4,4-dimethylcyclohexenyl) $=C(SO_2-C_6H_4-CH_3)(COOC_2H_5)$ |
| 2.5 | $CH_2=C(CH_3)-CO-NH-(CH_2)_3-COO-(CH_2)_2-HN-$ cyclohexenyl $=C(COOC_2H_5)_2$ |
| 2.6 | $C_2H_5-HN-$ (4,4-dimethylcyclohexenyl) $=C(CN)-COO-(CH_2)_2-O-CO-CH=CH_2$ |
| 2.7 | $C_2H_5-HN-$ cyclohexenyl $=C(SO_2-C_6H_4-CH=CH_2)(COOCH_3)$ |
| 2.8 | $C_3H_7-HN-$ cyclohexenyl $=C(CN)-CO-NH-CH_2-C_6H_4-CH=CH_2$ |

-continued

| No. | Formula |
|---|---|
| 2.9 | 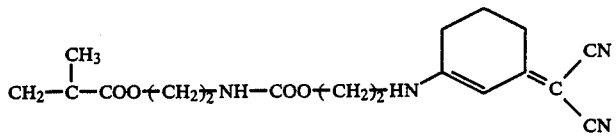 |

Compounds corresponding to formula (5) may be prepared and polymerized in known manner, optionally with copolymerisation with the usual comonomers, preferably acrylic acid esters, methacrylic acid esters or aromatic vinyl compounds. If desired, two or more comonomer compounds may be used together, e.g. n-butylacrylate and divinylbenzen, styrene and methyl methacrylate, or methacrylate and methacrylic acid.

The high molecular weight compound HM may be a poly-addition or polycondensation product containing urethane or ester linkages and having a recurrent group G derived from the UV absorbent structure of the general formula (1).

In a particularly preferred embodiment, the group G has the following structure (6):

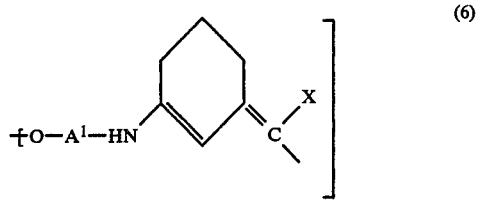

wherein
$A^1$ is a linking member, in particular an alkylene group with 1 to 20 carbon atoms (for example, a methylene group, an ethylene group, a trimethylene group, a 2-hydroxy-trimethylene group, a pentamethylene group, a hexamethylene group, an ethylene group, a propylene group or an arylene or cycloalkylene group, and X denotes an electron accepting group, in particular CN, $COOR^4$, $CONHR^4$, $COR^4$ or $SO_2R^4$, where $R^4$ has the meaning indicated above, and the group G is linked to the remainder of compound HN via the oxygen atom/or the free bond on the carbon atom which is substituted with X.

Specific compounds which are particularly preferred are given in the following Table 3:

| No. | Formula |
|---|---|
| 3.1 | 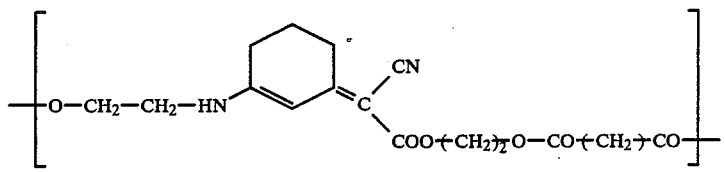 |
| 3.2 | 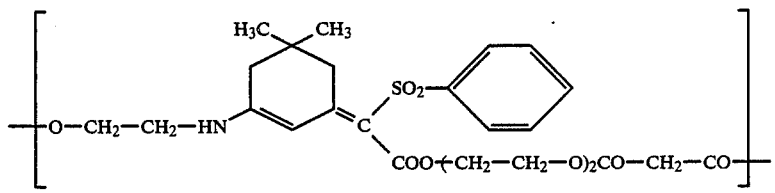 |
| 3.3 | 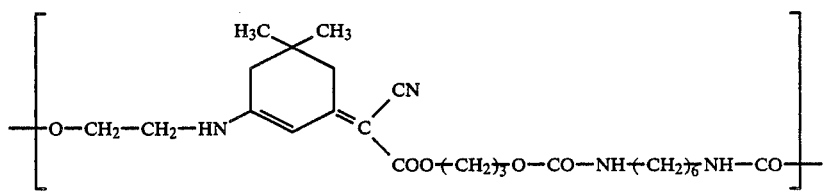 |

| No. | Formula |
|---|---|
| 3.4 | 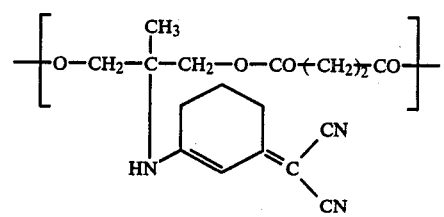 |
| 3.5 | 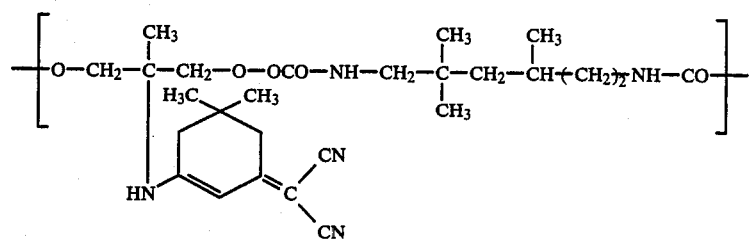 |
| 3.6 | 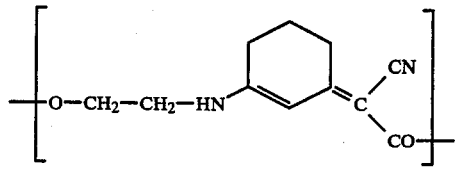 |
| 3.7 | 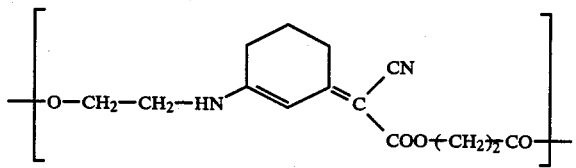 |

The molecular weights of compounds (6) according to the invention are preferably in the region of 500 to 5000. Compounds having higher molecular weights are also suitable but more difficult to prepare. Molecular weights in the range indicated above are generally sufficient to provide the necessary capacity for diffusion of the polyaddition or condensation products.

The polyesters according to the invention corresponding to formula (6) may be prepared by the known methods of polyester synthesis as described e.g. in Ullmanns Encyklopädie der technischen Chemie, 4th Edition, Volume 19, pages 61 et seq, Verlag Chemie, Weinheim. The starting materials used for the esterification are UV absorbent diols and dicarboxylic acids, activated dicarboxylic acids or dicarboxylic acid derivatives such as esters, acid chlorides, acid anhydrides, reaction products of carbodiimides and dicarboxylic acids, reaction products of dicarboxylic acids and 2-chloro-2-methyl-pyridinium iodide (Macromol. Chem. 185, 2347 (1984), or dicarboxylic acid imidazolides.

The polyurethanes corresponding to formula (6) may be synthesized by the polyaddition of UV absorbent diols with diisocyanates according to the process described in Ullmanns Encyklopädie der technischen Chemie, 4th Edition, Volume 19, pages 301 et seq. The processes of polyester synthesis and polyurethane synthesis may also be combined.

The compounds according to the invention may be prepared from 1-aminocyclohexenone-3 compounds corresponding to the formula

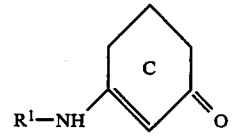

in which the substituents have the meanings already indicated. Compounds of this kind may readily be prepared by the condensation of dihydroxy resorcinols with amines and provide the compounds according to the invention in high yields after quaternization and reaction with malonic acid nitrile or other suitable methylene-active compounds. The preparation of compound 1.2 is described below by way of example and the other compounds may be obtained analogously:

1-(2-Ethylhexylamino)-5,5-dimethyl-cyclohexenone-3

A mixture of 65 g of ethyl hexylamine and 70 g of dimedone in 500 ml of toluene is stirred at room temperature for 2 hours and then heated for 3 hours with the use of a water separator. 8 g of water are separated. The toluene is evaporated off under vacuum and the oil left behind solidifies when cold to a crystal paste which may be used for further reaction without purification. The yield is virtually quantitative. Recrystallisation from cyclohexane: M.p. 68°–70° C.

Compound 1.2

125 g of 1-(2-Ethylhexylamino)-5,5-dimethylcyclohexenone-3 are slowly heated to 100° C. in an oil bath with 53 ml of dimethylsulphate and stirred for 40 minutes at this temperature after the reaction has slowed down. The reaction mixture is cooled to 60° C., 85 ml of isopropanol, 33 g of malonitrile and 75 ml of triethylamine are added, and the mixture is heated to 110° C. on an oil bath for 40 minutes. The mixture is then cooled and the compound is precipitated with water, suction filtered and recrystallised from acetonitrile. Yield: 127 g=79%, m.pt. 91°–95° C.

The compounds according to the invention may be dispersed in known manner for use in photographic materials. After dispersion in an aqueous gelatine solution, the organic solvent used for dissolving the compounds may be removed from the dispersion. The solvents should either be to some extent soluble in water so that they can be removed by washing the shredded dispersion or they should be capable of being removed by spray drying or vacuum or steam rinsing. Examples of organic solvents which can be removed include esters (for example. lower alkyl esters, etc.), lower alkyl ethers, ketones, halogenated hydrocarbons (for example, methylene chloride, trichloroethylene, etc.) fluorinated hydrocarbons, alcohols (for example, methyl to butyl alcohol) and combinations thereof.

Any type of dispersing agent may be used for dispersing the UV absorbents, but ionic surface-active agents and especially anionic surface-active agents are preferred. The quantity of dispersing agent used is preferably in the range of 2 to 15%, based on the quantity of compound used.

Ampholytic surface-active agents such as C-cetyl-betaine, N-alkylaminopropionates or N-alkyliminodipropionates, etc. may also be used.

A small quantity of permanent solvent, i.e. a water-immiscible organic solvent with high boiling point (i.e. above 200° C.) such as dibutylphosphate and/or tricresylphosphate, etc. may be used to improve the stability of the dispersion and the flexibility of the cast emulsion. The concentration of the permanent solvent must be sufficiently low to plasticize the polymer while keeping it in a state of solid particles. Furthermore, when using a permanent solvent it is important to keep the quantity of this solvent as small as possible in order to ensure that the layer of emulsion or hydrophilic colloid layer finally obtained will be sufficiently thin to provide a sharp image.

The compounds according to the invention may also be cast on a latex.

The photographic recording materials are preferably materials containing at least one light-sensitive silver halide emulsion layer and optionally other auxiliary layers.

The compounds according to the invention may be introduced, for example, into a layer of binder or into a light-sensitive silver halide emulsion layer. The silver halide emulsion layer may be subdivided into partial layers of the same spectral sensitivity but differing in the degree of sensitivity. The compounds to be used according to the invention may be introduced, for example, into a high-sensitivity blue-sensitive partial layer. In another preferred embodiment, the compounds are introduced into a UV filter layer arranged at the top of the photographic material above all the light-sensitive layers.

The quantity to be used depends on the purpose for which the compound is to be used and may easily be optimized by the usual methods. Preferred quantities, for example, are in the range of 50 to 1000 mg/m$^3$.

In addition to the layers already mentioned, the colour photographic recording material according to the invention may contain other, light-insensitive auxiliary layers, e.g. bonding layers. antihalation layers or covering layers, in particular interlayers placed between the light-sensitive layers to prevent the diffusion of developer oxidation products from one layer to another.

The light-sensitive silver halide emulsion layers preferably have associated colour couplers which react with the colour developer oxidation products to form a non-diffusible dye. The dyes are preferably accommodated in a non-diffusible form in the light-sensitive layer itself or closely adjacent thereto. It may in some cases be indicated to use at least some couplers which have a limited capacity for diffusion.

Thus, the red-sensitive layer, for example, may contain a non-diffusible colour coupler to produce the cyan partial colour image, generally a coupler of the phenol or α-naphthol series. The green-sensitive layer, for example, may contain at least one non-diffusible colour coupler to produce the magenta partial colour image, usually a colour coupler of the 5-pyrazolone series. The blue-sensitive layer may contain, for example, at least one non-diffusible colour coupler for producing the yellow partial colour image, generally a colour coupler having an open chain ketomethylene group. The colour couplers may be, for example, 6-, 4- or 2-equivalent couplers. Suitable couplers have been disclosed in the publications "Farbkuppler" by W. Pelz in "Mitteilungen aus den Forschungslaboratorien der Agfa, Leverkusen/München", Volume III, page 111 (1961), K. Venkataraman in "The Chemistry of Synthetic Dyes", Vol. 4, 341 to 387, Academic Press (1971) and T. H. James, "The Theory of the Photographic Process", 4th Edition, pages 353 to 362, and in the Journal "Research Disclosure" No. 17643, December 1978, Section VII, published by Industrial Opportunities Ltd., Homewell Havant, Hampshire, PO9 1 EF, Great Britain. The photographic material may also contain DIR compounds and white couplers which do not produce a dye when reacted with colour developer oxidation products. The inhibitors may be split off from the DIR compounds either on their own or by way of non-inhibitory intermediate compounds. See GB No. 953 454, U.S. Pat. Nos. 3,632,345, 4,248,962 and GB No. 2 072 363.

The halide contained in the light-sensitive silver halide emulsions used may be chloride, bromide, iodide or mixtures thereof. In a preferred embodiment the halide content of at least one layer consists of 0 to 12 mol-% of AgI, 0 to 50 mol-% of AgCl and 50 to 100% of AgBr. In a preferred embodiment, the halide consists predominantly of compact crystals, e.g. of a cubical, octahedral or transition form. The crystals are characterised in that their thickness is mainly greater than 0.2 μm. The average ratio of diameter to thickness is preferably less than 8:1, the diameter of a grain being defined as the diameter of a circle having a surface area equal to the projected surface of the grain. In another preferred embodiment, the silver halide crystals in some or all of the emulsions may be mainly tabular, with a ratio of diameter to thickness greater than 8:1.

The emulsions may be chemically sensitized with the usual sensitizing agents. Compounds containing sulphur, such as allylisothiocyanate, allylthiourea or thiosulphates are particularly preferred. Noble metals such as gold, platinum, palladium, iridium, ruthenium or rhodium and compounds of these noble metals are also suitable chemical sensitizers. This method of chemical sensitization has been described in the article by R. Koslowsky, Z. Wiss. Phot. 46, 65–72 (1951). The emulsions may also be sensitized with polyalkylene oxide derivatives. See also the abovementioned Research Disclosure No. 17643, Section III.

The emulsions may be optically sensitized in known manner, e.g. with the usual polymethine dyes such as neutrocyanines, basic or acid carbocyanines, rhodacyanines, hemicyanines, styryl dyes, oxonoles and the like. Sensitizers of this kind have been described by F. M. Hamer in "The Cyanine Dyes and related Compounds", (1964). See also in particular Ullmanns Enzyklopädie der technischen Chemie, 4th Edition, Volume 18, pages 431 et seq and the above-mentioned Research Disclosure No. 17643. Section IV.

The usual antifogging agents and stabilizers may be used in addition to the compounds according to the invention. Azaindenes are particularly suitable stabilizers, especially tetra- and penta-azaindenes and in particular those which are substituted with hydroxyl or amino groups. Compounds of this type have been described, for example, in the article by Birr, Z. Wiss. Phot. 47, 1952, pages 2–58. Other suitable stabilizers and anti-fogging agents are given in the above mentioned Research Disclosure No. 17643, in Section IV.

The constituents of the photographic material may be incorporated by the usual known methods. If the compounds are soluble in water or alkalies, they may be added in the form of aqueous solutions, optionally with the addition of water-miscible organic solvents such as ethanol, acetone or dimethylformamide. If they are insoluble both in water and in alkalies, they may be incorporated with the recording materials in a dispersed form in known manner. For example, a solution of these compounds in a low boiling organic solvent may either be mixed directly with the silver halide emulsion or it may first be mixed with an aqueous gelatine solution, the organic solvent being then removed, whereupon the resulting dispersion of the given compound may be mixed with the silver halide emulsion. So-called oil formers may also be added. These are generally relatively high boiling organic compounds in which the compounds to be dispersed are enclosed in the form of oily droplets. See, for example, U.S. Pat. Nos. 2,322,027, 2,533,514, 3,689,271, 3,764,336 and 3,765,897. Couplers may also be incorporated, e.g. in the form of charged latices, see DE-OS No. 2 541 274 and EP-A No. 14 921. The constituents may also be fixed in the material as polymers, see e.g. DE-OS No. 2 044 992, U.S. Pat. Nos. 3,370,952 and 4,080,211.

The usual layer supports may be used for the materials according to the invention. e.g. supports of cellulose esters such as cellulose acetate and of polyesters. Paper supports are also suitable, and these may be coated, e.g. with polyolefines, in particular with polyethylene or polypropylene. See the above-mentioned Research Disclosure No. 17,643, Section XVII.

The usual hydrophilic film forming substances may be used as protective colloids or binders for the layers of the recording material, e.g. proteins, in particular gelatine. See the binders listed in the above mentioned Research Disclosure No. 17,643, Section IX.

The layers of the photographic material may be hardened in the usual manner, for example with hardeners of the type of epoxides, heterocyclic ethylene imine or acryloyl. The layers may also be hardened by the process according to German Offenlegungsschrift No. 2 218 009 to produce colour photographic materials suitable for high temperature processing. The photographic layers or colour photographic multilayered materials may also be hardened with hardeners of the diazine, triazine or 1,2-dihydroquinoline series or with vinyl sulphone type hardeners. Other suitable hardeners are disclosed in German Offenlegungsschriften Nos. 2 439 551, 2 225 230 and 2 317 672 and in the above mentioned Research Disclosure 17,643, Section XI.

Other suitable additives are mentioned in Research Disclosure 17,643 and in "Product Licensing Index" of December 1971, pages 107–110.

Suitable colour developer substances for the material according to the invention include in particular those of the p-phenylenediamine series, e.g. 4-amino-N,N-diethylaniline hydrochloride; 4-amino-3-methyl-N-ethyl-N-β-(methanesulphonamido)-ethyl aniline sulphate hydrate; 4-amino-3-methyl-N-ethyl-N-β-hydroxyethylaniline sulphate; 4-amino-N-ethyl-N-(2-methoxyethyl)-m-toluidine-di-p-toluene sulphonic acid and N-ethyl-N-β-hydroxyethyl-p-phenylenediamine. Other suitable colour developers have been described. for example, in J. Amer. Chem. Soc. 73, 3100 (1951) and in G. Haist, Modern Photographic Processing, 1979, John Wiley and Sons, New York, pages 545 et seq.

The material is normally bleached and fixed after colour development. Bleaching and fixing may be carried out separately or together. The usual compounds may be used as bleaching agents, e.g. $Fe^{3+}$ salts and $Fe^{3+}$ complex salts such as ferricyanides, dichromates, water-soluble cobalt complexes, etc. Iron-III complexes of amino polycarboxylic acids are particularly preferred, in particular, for example, ethylene diaminotetracetic acid, nitrilotriacetic acid, iminodiacetic acid, N-hydroxyethylethylenediamino-triacetic acid, alkyliminodicarboxylic acids and corresponding phosphonic acids. Persulphates are also suitable bleaching agents.

The comparison compounds given in the following Examples have the following structure:

Comparison compound A:

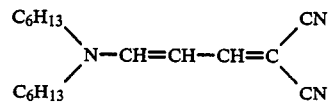

Comparison compound B:

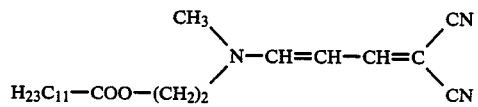

EXAMPLE 1

Compound 1.5 was dispersed in gelatine according to the general method described below. The dispersion obtained was applied to a transparent triacetate film in a quantity providing 0.2 mmol of the UV absorbent and 0.6 g of gelatine for each 1 $m^2$ of surface. The absorption spectrum was then determined. A layer containing no UV absorbent was then used as reference. 0.2 mmol of Compound 1.8 and a mixture of 20% of Compound 1.7 and 80% of Compound 1.2 were then also applied to triacetate films in the same manner as Compound 1.5. 0.2 mmol of Compounds A and B were used for comparison. General method of dispersion:

10 g of UV absorbent were dissolved with 10 g of tricresyl phosphate and 30 ml of ethyl acetate at 55° C. and dispersed with the aid of a dispersing agent in 150 ml of 7.5% gelatine which had also been heated to 55° C. The dispersion obtained was then freed from ethyl acetate under vacuum and solidified at 6° C.

The spectra in FIG. 1 show that the new type of UV absorbent has a marked maximum in the longwave UV region with a steeply descending longwave flank whereas the comparison compounds have a lower extinction with broader absorption band combined with a less steeply descending flank, which in practice may lead to loss of sensitivity and increase in $D_{min}$. The graphs in FIG. 1 represent the following:

Graph 5: Material containing UV absorbent 1.5
Graph 8: Material containing UV absorbent 1.8
Graph 7/2: Material containing a mixture of UV absorbents 1.7 and 1.2
Graph A: Material containing comparison UV absorbent A
Graph B: Material containing comparison UV absorbent B.

EXAMPLE 2

The following highly sensitive colour negative materials were prepared by applying the layers described below to a conventional layer support:

1st Layer: Antihalation layer containing colloidal silver, gelatine and an octyl hydroquinone
2nd Layer: Interlayer
3rd Layer: Red-sensitive, low sensitivity silver iodobromide emulsion layer containing a conventional cyan coupler, a DIR coupler and a red masking coupler
4th Layer: Red sensitive, high sensitivity silver iodobromide emulsion (10 mol-% iodide) and the cyan coupler indicated in Layer 3.
5th Layer: Interlayer containing gelatine and an octyl hydroquinone
6th Layer: Green-sensitive, low sensitivity silver iodobromide layer (5 mol-% silver bromide) containing a magenta coupler, a yellow masking coupler and a DIR coupler
7th Layer: Green-sensitive, high sensitivity silver iodobromide layer (9 mol-% iodide) containing the magenta and masking couplers mentioned in Layer 6.
8th Layer: Interlayer containing gelatine and an octyl hydroquinone
9th Layer: Filter yellow layer containing colloidal silver
10th Layer: Blue sensitive, low sensitivity silver iodobromide emulsion layer (6 mol-% iodide) and 1.05 g per m² of a conventional yellow coupler.
Silver application: corresponding to 1.0 g of silver nitrate per m²
11th Layer: Blue-sensitive, highly sensitive silver iodobromide layer (8.5 mol-% silver iodide) and 0.26 g per m² of a conventional yellow coupler.
Silver application: corresponding to 0.8 g of silver nitrate per m²
12th Layer: UV absorbent layer
13th Layer: Protective layer containing gelatine and a carbamoyl pyridinium salt as hardener.

The above mentioned layers also contain other components in addition to those mentioned above.

0.2 mmol of compounds 1.2, 1.4, 1.5, 1.6 and 1.8 and of comparison compounds A and B were incorporated in UV absorbent layer 12 in accordance with the formulation given in Example 1.

The materials prepared were used to photograph a yellow object colour having the remission spectrum shown in FIG. 2. A grey wedge adjusted to neutral was photographed at the same time. After development by the process described by E. Ch. Gehret, in Brit. J. of Photography 1974, page 567, the negative was copied on a conventional colour photographic paper. To enable a comparison to be made, exact grey copies of the prints obtained were made by means of the photographed grey wedge. The prints of the object colour which was photographed at the same time were then measured with a reflection view densitometer, Model Maobeth RD 400 equipped with a Wratten Filter No. 47. The summary given below shows that the UV absorbents according to the invention give rise to a higher yellow density of the yellow object colour reproduced in the copy, i.e. better colour saturation than the comparison compounds without increase in $D_{min}$ and without sensitivity loss.

| UV absorbent applied (No.) | | Neg. Sens.* (log H) | $D_{min}$ | Density/yellow in the copy |
|---|---|---|---|---|
| none | | −3.75 | 0.84 | 0.85 |
| 1.2 | according to the invention | −3.65 | 0.85 | 1.38 |
| 1.4 | according to the invention | −3.67 | 0.85 | 1.36 |
| 1.5 | according to the invention | −3.66 | 0.84 | 1.32 |
| 1.6 | according to the invention | −3.67 | 0.84 | 1.35 |
| 1.8 | according to the invention | −3.64 | 0.85 | 1.43 |
| A | Comparison | −3.62 | 0.87 | 1.25 |
| B | Comparison | −3.64 | 0.86 | 1.31 |

*An increase of 0.3 log H corresponds to a regression to half the sensitivity.

We claim:

1. Photographic elements containing at least one light-sensitive silver halide emulsion layer and at least one UV-absorbent, in an amount of from 50 to 1000 mg/m², said absorbent having the formula $$\begin{array}{c} R^2 \quad R^3 \\ \diagdown \diagup \\ C \\ \diagup \quad \diagdown \\ CH_2 \quad CH_2 \quad CN \\ | \quad | \quad \diagup \\ R^1-NH-C \quad C=C \\ \diagdown \diagup \quad \diagdown \\ CH \quad Y \end{array}$$

wherein
$R^1$ denotes a saturated aliphatic hydrocarbon group with 1 to 24 carbon atoms unsubstituted or substituted by alkoxy or aryloxy
$R^2$, $R^3$ which may be identical or different, denote hydrogen or an alkyl group with 1 to 4 carbon atoms,
Y denotes CN, $COOR^4$, $CONHR^4$, $COR^4$ or $SO_2R^4$, and
$R^4$ denotes an alkyl group with 1 to 18 carbon atoms or aralkyl with 7 to 15 carbon atoms or aryl.

2. Photographic elements as claimed in claim 1, characterised in that the UV absorbent is contained in a light-sensitive silver halide emulsion layer.

3. Photographic elements as claimed in claim 1, characterised in that the UV absorbent is contained in a light-insensitive filter layer.

* * * * *